US008603054B2

(12) United States Patent
Lemke et al.

(10) Patent No.: US 8,603,054 B2
(45) Date of Patent: Dec. 10, 2013

(54) DELIVERY PRODUCT FOR TOPICAL COMPOSITIONS

(75) Inventors: Sarah Anne Lemke, Appleton, WI (US); Kroy Donald Johnson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/361,696

(22) Filed: Jan. 30, 2012

(65) Prior Publication Data

US 2012/0130323 A1 May 24, 2012

Related U.S. Application Data

(63) Continuation of application No. 12/164,872, filed on Jun. 30, 2008, now abandoned.

(51) Int. Cl.
*A61F 13/15* (2006.01)
*A61F 13/511* (2006.01)

(52) U.S. Cl.
USPC ........... 604/304; 604/358; 604/359; 604/360; 604/382; 424/401; 424/402

(58) Field of Classification Search
USPC ..................... 604/358, 359, 360, 382, 386.06
See application file for complete search history.

(56) References Cited

U.S. PATENT DOCUMENTS

| | | | |
|---|---|---|---|
| 3,419,593 A | 12/1968 | Willing | |
| 3,715,334 A | 2/1973 | Karstedt | |
| 3,814,730 A | 6/1974 | Karstedt | |
| 3,923,705 A | 12/1975 | Smith | |
| 4,100,324 A | 7/1978 | Anderson et al. | |
| 4,323,534 A | 4/1982 | DesMarais | |
| 4,663,220 A | 5/1987 | Wisneski et al. | |
| 4,704,116 A | 11/1987 | Enloe | |
| 4,834,738 A | 5/1989 | Kielpikowski et al. | |
| 4,940,464 A | 7/1990 | Van Gompel et al. | |
| 5,093,422 A | 3/1992 | Himes | |
| 5,262,055 A | 11/1993 | Bae et al. | |
| 5,284,703 A | 2/1994 | Everhart et al. | |
| 5,304,599 A | 4/1994 | Himes | |
| 5,332,613 A | 7/1994 | Taylor et al. | |
| 5,350,624 A | 9/1994 | Georger et al. | |
| 5,766,389 A | 6/1998 | Brandon et al. | |
| 6,498,284 B1 | 12/2002 | Roe | |
| 6,645,190 B1 | 11/2003 | Olson et al. | |
| 6,689,932 B2 | 2/2004 | Kruchoski et al. | |
| 6,749,860 B2 | 6/2004 | Tyrrell et al. | |
| 6,756,520 B1 | 6/2004 | Krzysik et al. | |
| 6,989,471 B2 | 1/2006 | Schmidt et al. | |
| 7,005,557 B2 | 2/2006 | Klofta et al. | |
| 7,060,867 B2 | 6/2006 | Jameson | |
| 7,264,615 B2 | 9/2007 | Sherrod | |
| 7,780,979 B2 | 8/2010 | Hu et al. | |
| 2001/0009991 A1 | 7/2001 | Hisanaka | |
| 2001/0021833 A1 | 9/2001 | Schmidt et al. | |
| 2002/0143316 A1* | 10/2002 | Sherrod et al. | 604/385.101 |
| 2003/0204180 A1 | 10/2003 | Huang et al. | |
| 2003/1013580 | 10/2003 | Huang | |
| 2004/0127877 A1* | 7/2004 | Odorzynski et al. | 604/385.03 |
| 2005/0124957 A1* | 6/2005 | Giloh | 604/385.03 |
| 2006/0002987 A1 | 1/2006 | Bevacqua et al. | |
| 2006/0135911 A1* | 6/2006 | Mittur | 604/113 |
| 2006/0286152 A1 | 12/2006 | Hu et al. | |
| 2009/0022700 A1 | 1/2009 | Cassin | |
| 2009/0275906 A1 | 11/2009 | Berland | |

FOREIGN PATENT DOCUMENTS

| | | |
|---|---|---|
| EP | 1371379 | 12/2003 |
| EP | 1 757 279 | 2/2007 |
| WO | 97/24150 | 7/1997 |
| WO | WO9724150 | 7/1997 |
| WO | WO0010500 | 3/2000 |
| WO | 00/37009 | 6/2000 |
| WO | WO02051456 | 7/2002 |
| WO | WO 2007038966 A1 * | 4/2007 |
| WO | WO2007073246 | 6/2007 |
| WO | WO2008054268 | 5/2008 |

OTHER PUBLICATIONS

Search Report and Written Opinion for PCT/IB2009/052013, Dated Jan. 19, 2010.
Search Report and Written Opinion for Application No. PCT/IB2009/052013, dated Jan. 19, 2010.

* cited by examiner

*Primary Examiner* — Gina C Justice
(74) *Attorney, Agent, or Firm* — Dority & Manning, P.A.

(57) ABSTRACT

A delivery product is used to deliver a skin composition to the skin of a user. The delivery product includes a thermo-responsive polymer film. The polymer film is solid at room temperature but, once contacted with the skin, increases in temperature and degrades. A skin composition is associated with the polymer film. The skin composition can be applied to a surface of the film or can be incorporated into the film. The skin composition is released by the polymer film for treating the skin of the user.

22 Claims, 6 Drawing Sheets

DELIVERY PRODUCT FOR TOPICAL COMPOSITIONS

RELATED APPLICATIONS

The present application is a continuation application and claims priority to U.S. patent application Ser. No. 12/164,872, filed on Jun. 30, 2008 now abandoned, which is incorporated herein by reference.

BACKGROUND

There are a variety of products that are applied topically to the skin. Some products are applied to the skin, for instance, for cosmetic purposes or in order to otherwise provide a benefit to the skin. Other topical skin compositions are applied to the skin in order to treat an ailment or skin condition. For example, various diaper rash creams are available that are designed to either treat a diaper rash or to otherwise relieve symptoms caused by diaper rash.

Many topical skin compositions are applied to the skin in the form of a cream, lotion or gel. These products, for instance, are typically applied to one's hand or to an applicator and then applied to the area of the skin where the topical composition is desired. In many instances, however, the skin to be treated is fragile or easily irritated when touched. In addition, applying topical compositions by hand can be messy in some circumstances and creating waste by leaving some of the composition on the hands of the user or on an applicator.

In view of the above, a need currently exists for a delivery device capable of applying topical compositions to the skin that avoids the messes and inefficiencies commonly associated with creams and lotions. A need also exists for a delivery device capable of applying a topical composition to the skin in a careful and controlled manner that does not irritate the area where the topical composition is applied.

SUMMARY

In general, the present disclosure is directed to a delivery product for a topical skin composition. The delivery product can be used to apply any suitable composition to the skin, such as any skin care active or medicament. Of particular advantage, the topical composition can be applied to the skin without having to touch or rub the skin with one's hand. The delivery product can also be tailored so as to release any active ingredients contained in the topical composition over a desired period of time.

For example, in one embodiment, the delivery product includes a thermo-responsive polymer film. The thermo-responsive polymer film is solid at ambient temperature, such as at a temperature of 23° C. The thermo-responsive polymer film, however, contains a material that changes properties when increased in temperature. For example, in one embodiment, the film may contain a polymer that changes properties at a temperature greater than 23° C. and less than the normal body temperature of an individual, such as about 37° C. For example, in one embodiment, a material such as a polymer may be present in the film that changes properties at a temperature of from about 30° C. to about 37° C. When the material changes properties, the thermo-responsive polymer film degrades. As used herein, the term degrade means that the polymer film loses its structural integrity. For example, the polymer film may disintegrate into smaller pieces, turn into a liquid, be absorbed by the skin, or be absorbed into an adjacent garment.

In accordance with the present disclosure, the delivery product further includes a topical skin composition in association with the thermo-responsive polymer film. For example, the topical composition may be incorporated into the polymer film, may be applied to a surface of the polymer film, or otherwise attached to or connected to the film. The topical skin composition can contain, for example, a skin care active, a medicament, or mixtures thereof.

The delivery product is used by applying the thermo-responsive polymer film to the skin of a user. The film, for instance, can be applied directly to the skin or, alternatively, can be placed in an absorbent article for contact with the skin when the article is donned. Once contacted with the skin, the thermo-responsive polymer film increases in temperature due to absorbing body heat. Consequently, the thermo-responsive polymer film degrades releasing the topical skin composition or otherwise disassociating from the topical skin composition.

In one embodiment, the thermo-responsive polymer film can be made from any suitable polymer or mixture of polymers that are solid at room temperature and then sensitive to temperature increases that cause the delivery product to degrade when contacted with a person's skin. Examples of polymers that may be used, for instance, include chitosan, polyacrylic acid or derivatives, a N,N-dialkylacrylamide copolymer, a wax such as a paraffin wax, mixtures thereof, and the like. In one embodiment, the thermo-responsive polymer film is substantially water insoluble. Thus, delivery of the topical composition can be controlled exclusively by temperature. When water insoluble, the delivery product can continue to release the topical composition even after being wetted.

The topical skin composition contained in the polymer film can change dramatically depending upon the particular application. In general, any suitable composition that is be applied to the skin can be used. Without limitation, for instance, examples of skin care actives and medicaments that may be incorporated into the topical skin composition include antibacterial agents, deodorants, skin moisturizers, cleansers, anti-itch agents, cooling agents, diaper rash agents, and the like. Further, it should be understood that the topical skin composition can also contain mixtures of different skin care actives and medicaments. For instance, an anti-itch agent may be combined with other medicaments that serve as active agents to treat the skin.

In addition to the delivery product itself, the present disclosure is also directed to a system for delivering a topical skin composition. The system can include, for instance, an absorbent article configured to be placed adjacent to the skin of a wearer. The absorbent article may include an interior surface that is placed adjacent to the skin and an opposite exterior surface. The system can further comprise an insert that is separate from the absorbent article but can be manually positioned on the interior surface of the absorbent article for contact with the wearer's skin in the desired area. The insert, for instance, may comprise the delivery product as described above.

In general, any suitable absorbent article can be used with the insert. The absorbent article may comprise, for instance, a diaper, a training pant, absorbent swimwear, feminine hygiene pads, an adult incontinence product, or a wound dressing.

In one embodiment, the insert to be used with the absorbent article can include the thermo-responsive polymer film laminated to a releasable backing layer. The releasable backing layer, for instance, can be configured to be separated from the polymer film when the polymer film is applied to the absorbent article.

Of particular advantage, the delivery product can be made so as to adhere to the skin or can be used in conjunction with the absorbent article so that no adhesive, such as a body adhesive, is necessary for maintaining contact between the polymer film and the skin of the user. The thermo-responsive polymer film can also be tailored to degrade over a desired period of time. In one embodiment, for instance, the thermo-responsive polymer film may be constructed so that if the film is placed on a surface at a temperature of 34° C. in an ambient environment, the film takes at least 30 minutes to complete degrade.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
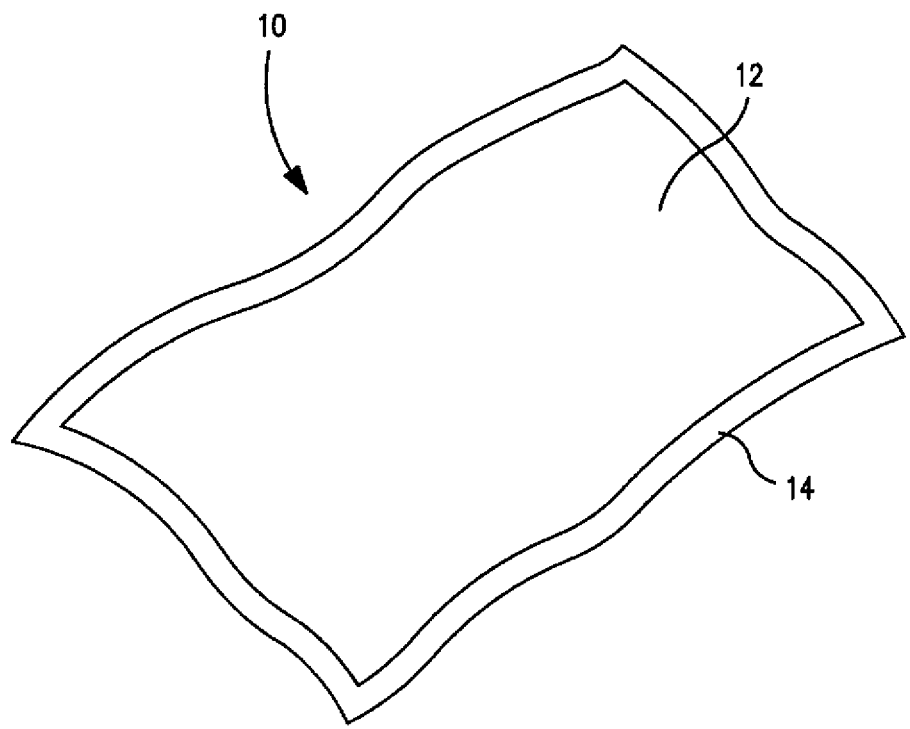
FIG. 1 is a perspective view of one embodiment of a delivery product made in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

In general, the present disclosure is directed to a delivery product for topical skin compositions. The delivery product comprises a thermo-responsive polymer film that is solid at ambient temperatures, such as at 23° C. The thermo-responsive film is placed in association with a topical skin composition that is intended to contact the skin for providing some benefit. In accordance with the present disclosure, the thermo-responsive film is constructed such that, when contacted with the skin of a user, the film increases in temperature due to the transfer of body heat and then degrades once heated to a certain temperature. As the polymer film degrades or prior to degrading, the topical skin composition is released for interaction with the skirt.

The skin delivery product of the present disclosure can provide various advantages and benefits. For example, the delivery product can provide a gentle method for applying skin compositions to fragile, compromised or damaged skin that is sensitive to the touch, torn or bruised easily.

Although the delivery product may be used alone, in one embodiment, the delivery product may be used in conjunction with an absorbent article. For instance, the delivery product may be placed within an absorbent article in order to not only deliver a topical composition to the skin but may also assist in treating hard to reach areas such as in the perineal region. For example, by placing the delivery device in an absorbent article, the skin composition is applied by donning the article making the delivery product particularly well suited for use by those with compromised dexterity or strength, especially when the skin composition is to be applied to areas not easily accessible by hand. Applying the delivery product in association with an absorbent article is also a very delicate and gentle way to deliver a skin composition to those with fragile skin, such as the elderly, and those that have skin problems related to conditions such as diabetes.

In one embodiment, the delivery product is maintained separate from the absorbent article and used as an insert when desired. Thus, a caregiver or wearer of the absorbent article can choose when to apply the delivery product and to only use the delivery product when needed.

Also of advantage is that the delivery product can treat the skin of a user with a skin composition without any related mess. For example, skin compositions in the form of gels, pastes and creams are typically applied to the skin by first applying the composition onto one's hand. After application, some of the composition remains on the hand which not only requires the hands to be cleaned but also represents wasted material. Spray applicators also tend to cover more than the desired area creating waste. The delivery product of the present disclosure, on the other hand, avoids the above problems.

As will be described in greater detail below, the delivery product of the present disclosure can also be tailored to deliver a skin composition over a desired duration of time. For instance, the thermo-responsive film can be formulated and constructed so as to degrade either quickly or relatively slowly based upon the film chemistry. Topical compositions, on the other hand, must be reapplied at periodic intervals in order to achieve the same effect.

Referring to FIG. 1, one embodiment of a delivery product 10 made in accordance with the present disclosure is shown. As illustrated, the delivery product 10 includes a thermo-responsive film 12 associated with a topical skin composition. Optionally, the thermo-responsive film 12 can be associated with one or more releasable backing layers, such as backing layer 14. The backing layer 14 is configured to be removed from the thermo-responsive polymer film 12 when the film is applied to the skin or to an absorbent article. In the embodiment illustrated in FIG. 1, a single backing layer 14 is shown. In alternative embodiments, however, the thermo-responsive film 12 may be positioned in between two opposing backing layers.

The backing layer 14, for instance, can be made from any suitable material capable of protecting the thermo-responsive film while easily separating from the film. The backing layer 14, for instance, may comprise a polymer film or paper layer coated with a release material, such as a silicone or wax.

The thermo-responsive polymer film 12 is generally made from one or more polymers. At least one material contained in the film is temperature sensitive such that the film changes properties when heated. The material can be a polymer used to form the film or another material present in the polymer matrix.

More particularly, the thermo-responsive film 12 made according to the present disclosure is constructed such that the film is a solid at ambient temperature, which is typically about 23° C. The thermo-responsive film, however, is also constructed such that the film begins to degrade at close to body temperature. The term "body temperature" is the temperature at the skin's surface of a user. For humans, the body temperature is typically about 34° C.±3° C. Thus, body temperature can be from about 31° C. to about 37° C. Consequently, the thermo-responsive polymer film is constructed such that the film will begin to degrade at a temperature of greater than 23° C. but less than about 34° C. For example, in one embodiment, the thermo-responsive polymer film may be constructed such that the film degrades at a temperature of from about 27° C. to about 34° C., and particularly from about 29° C. to about 31° C.

In this manner, once the thermo-responsive polymer film is applied to the skin, the film absorbs the heat being given off by the skin and increases in temperature to approximately the body temperature of the user. Once heated to a particular threshold temperature, the film then degrades. The topical skin composition associated with the film can be released from the film upon contact with the skin or may be released from the film as the film degrades.

The thermo-responsive polymer film can degrade in various ways. For instance, in one embodiment, the thermo-responsive polymer film may convert to a liquid when heated above ambient temperatures. In an alternative embodiment, the film may simply disintegrate into smaller particles. In still another embodiment, the film may degrade and be absorbed by the skin. In yet another embodiment, the film may degrade and be absorbed into the clothing of the user or into an absorbent article associated with the product.

In one embodiment, the thermo-responsive polymer film contains at least one or more temperature sensitive polymers. In general, any suitable temperature sensitive polymer may be used that is capable of being a solid at ambient temperature but changing physical properties at the temperature ranges described above. Examples of some polymers that may be used to construct the film may include, for instance, any suitable wax. The wax, for instance, may comprise a paraffin wax that changes from a solid to a liquid when heated above ambient temperature.

Other exemplary materials that may be used include a chitosan, a polyacrylic acid or derivative, a N,N-dialkylacrylamide copolymer or blend, and the like.

In one embodiment, the thermo-responsive polymer film may be made from a thermo-responsive polymer that is an interpenetrating polymer network. Suitable interpenetrating polymer networks may be formed, for instance, from a polyacrylic acid and a block copolymer. The block copolymer, for instance, may be a polyethylene oxide/polypropylene oxide block copolymer. Another embodiment of an interpenetrating polymer network may be formed from a random copolymer of a methyacrylamide derivative and a comonomer to form a thermally reversible solid at room temperature. The random copolymer may be in the form of a plurality of linear chains having a plurality of molecular weights greater than or equal to a minimum gelling molecular weight cutoff.

In still another embodiment, an interpenetrating polymer network may be used that comprises a reversible solid based on NiPAAM and copolymers that do not reverse upon dilution. Such polymers are described, for instance, in U.S. Pat. No. 5,262,055, which is incorporated herein by reference.

Another example of an interpenetrating polymer network may comprise polymethylvinyl ether families. In still another embodiment, the polymer network may be formed from a cationic chitosan made thermally sensitive by the addition of a salt, such as polyol salts (β-glycerophosphate).

In one embodiment, the thermo-responsive polymer film may contain a phase change component alone or in combination with other materials that causes the film to degrade when heated near body temperature. Phase change components that may be used include LURAPRET® phase change powder, a purified, encapsulated paraffin available from BASF Corporation of New Jersey, hydrocarbons (e.g., straight chain alkanes or paraffinic hydrocarbons, branched-chain alkanes, unsaturated hydrocarbons, halogenated hydrocarbons, and alicyclic hydrocarbons), waxes, oils, fatty acids, fatty acid esters, dibasic acids, dibasic esters, 1-halides, primary alcohols, aromatic compounds, anhydrides (e.g., stearic anhydride), ethylene carbonate, polyhydric alcohols (e.g., 2,2-dimethyl-1,3-propanediol, 2-hydroxymethyl-2-methyl-1,3-propanediol, ethylene glycol, polyethylene glycol, pentaerythritol, dipentaerythritol, pentaglycerine, tetramethylol ethane, neopentyl glycol, tetramethylol propane, monoaminopentaerythritol, diaminopentaerythritol, and tris(hydroxymethyl)acetic acid), polymers (e.g., polyethylene, polyethylene glycol, polypropylene, polypropylene glycol, polytetramethylene glycol, and copolymers, such as polyacrylate or poly(meth)acrylate with alkyl hydrocarbon side chain or with polyethylene glycol side chain and copolymers comprising polyethylene, polyethylene glycol, polypropylene, polypropylene glycol, or polytetramethylene glycol), and mixtures thereof.

Using a thermo-responsive polymer film as described above can provide various advantages in particular applications. For example, although many of the materials described above are temperature sensitive, the film can be constructed so as to be substantially water insoluble. Thus, the films will only degrade when elevated in temperature and will resist degrading when contacted with moisture. The films may contact moisture, for instance, from the surface of the skin or from the environment in which they are used. When used in an absorbent article, the delivery product may contact body fluids without degrading and still delivering the skin composition. This feature makes the delivery product particularly well suited for use in diapers and adult incontinence products for treating skin ailments, such as diaper rash.

The thermo-responsive polymer film in addition to being water insoluble can be constructed so as to degrade over a desired period of time by changing or altering the components and their relative amounts. For example, in one embodiment, the thermo-responsive polymer film can be configured to degrade very quickly (such as less than about 10 minutes) when elevated in temperature. Alternatively, polymers and other materials can be chosen to form the film that cause the film to degrade relatively slowly. For example, in one embodiment, a thermo-responsive polymer may be combined with a polymer that is not temperature sensitive in forming the film. In one embodiment, for instance, the thermo-responsive polymer film may be constructed such that when the product is placed on a surface at a temperature of 34° C. in an ambient environment, the film takes at least 30 minutes, such as at least 40 minutes, such as at least 60 minutes, such as from about 30 minutes to about 120 minutes to completely degrade.

In addition to the thermo-responsive polymer film, the delivery product of the present disclosure includes a topical skin composition associated with the film. The topical skin composition can be associated with the film in various different ways. For example, in one embodiment, the skin composition can be incorporated into the film. In this manner, the skin composition is embedded in the film and is released as the film degrades.

Alternatively, the skin composition can be coated on the film. In this embodiment, the composition is immediately released to the skin as the film degrades.

In still another embodiment, a skin composition may be incorporated into the film while a second skin composition may be applied to the film as a coating.

The thermo-responsive polymer film can be used to deliver any suitable skin composition depending upon the particular application and the desired result. Particular examples of materials or ingredients that may be included in the skin composition include any suitable skin care active, medicament, or mixtures thereof. Particular components contained in the composition may include, for instance, antibacterial agents, deodorants, skin moisturizers, skin cleansers, anti-itch agents, cooling agents, diaper rash agents, or mixtures thereof.

Other ingredients or components that may also be contained within the delivery product include antioxidants (product integrity); anti-reddening agents, such as aloe extract; astringents—cosmetic (induce a tightening or tingling sensation on skin); astringents—drug (a drug product which checks oozing, discharge, or bleeding when applied to skin or mucous membrane and works by coagulating protein); biological additives, including botanical chemicals and proteins (enhance the performance or consumer appeal of the product); external analgesics (a topically applied drug that has a topical analgesic, anesthetic, pain reliever or antipruritic effect by depressing cutaneous sensory receptors, of that has a topical counterirritant effect by stimulating cutaneous sensory receptors); hydrotropes (helps dissolve some antimicrobial agents); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); natural moisturizing factors, amino acids, anti-inflammatory agents, sunscreens, insect repellants, antiperspirants, vitamins (e.g. Vitamin B, C or E), and the like.

In one embodiment, the topical skin composition may be for moisturizing the skin and may contain a humectant. Humectants are typically cosmetic ingredients used to increase the water content of the top layers of the skin or mucous membrane, by helping control the moisture exchange between the product, the skin, and the atmosphere. Humectants may include primarily hydroscopic materials. Suitable humectants include urocanic acid, N-Acetyl ethanolamine, aloe vera gel, arginine PCA, chitosan PCA, copper PCA, Corn glycerides, dimethyl imidazolidinone, fructose, glutamine, glucose, glucose glutamate, glucuronic acid, glutamic acid, glycereth-7, glycereth-12, glycereth-20, glycereth-26, glycerin, honey, hydrogenated honey, hydrogenated starch hydrolysates, hydrolyzed corn starch, lactamide MEA, lactic acid, lactose lysine PCA, mannitol, methyl gluceth-10, methyl gluceth-20, PCA, PEG-2 lactamide, PEG-10 propylene glycol, polyamino acids, polysaccharides, polyamino sugar condensate, potassium PCA, propylene glycol, propylene glycol citrate, saccharide hydrolysate, saccharide isomerate, sodium aspartate, sodium lactate, sodium PCA, sorbitol, TEA-lactate, TEA-PCA, Urea, Xylitol, and the like and mixtures thereof. Preferred humectants include polyols, glycerin, ethoxylated glycerin, polyethylene glycols, hydrogenated starch hydrolysates, propylene glycol, silicone glycol, pyrrolidone carboxylic acid and mixtures thereof.

In one embodiment, the topical skin composition may contain a surfactant that promotes emulsifying activity. Surfactants have the ability to lower the surface tension of water to reduce the interfacial tension between two immiscible substances. Surfactants can also enhance cleaning or removal of dirt, sweat, and/or sebum from the skin. Some surfactants may also act as a wetting agent to facilitate absorption of other components. As examples, surfactants may be selected from groups of sorbitan fatty acids (sorbitan monopalmitate, sorbitan monolaurate and the like), polyoxyethylene sorbitan fatty acid esters (polyoxyethylene 20 sorbitan monolaurate, polyoxyethylene sorbitan 20 monostearate, polyoxyethylene 4 sorbitan monostearate and the like), polyoxyethylene acids (polyoxyethylene 8 stearate, polyoxyethylene 20 stearate, and the like), and polyoxyethylene alcohols (polyoxyethylene 4 lauryl ether, polyoxyethylene 10 cetyl ether, polyoxyethylene 10 stearyl ether, polyoxyethylene 5.5 decyl ether, and the like), but the surfactant(s) can be selected from any suitable surfactants.

As described above, in one embodiment, a cooling agent may be incorporated into the skin composition. Cooling agents cool the skin by various techniques, such as by evaporation. For example, water may serve as a cooling agent. Suitable cooling agents that may be used include water; hydrocarbons such as isododecane and isoeicosane; short chain alcohols such as ethanol and n-propanol; small branched chain alcohols such as isopropyl alcohol; fluorinated hydrocarbons such as perfluorodecalin, perfluoroheptane, perfluorohexane, and perfluoromethylcyclohexane; fluorinated alcohols such as C6-C12 perfluoroalkylethanol and perfluorocyclohexylmethanol; fluorinated ethers such as ethyl perfluorobutyl ether, ethyl perfluoroisobutyl ether, methyl perfluorobutyl ether, methyl perfluoroisobutyl ether, and perfluorohexylethyl dimethylbutyl ether; low molecular weight grades of dimethicone, particularly DOW CORNING® 200 dimethicone fluid 0.65 cst; volatile cyclomethicones such as octamethyl cyclotetrasiloxane, decamethyl cyclopentasiloxane, dodecamethyl cyclohexasiloxane, and tetradecamethyl cycloheptasiloxane.

Another particular ingredient that may be present in the skin composition is a liquid powder. Liquid powders create a silky and powdery feel on the skin. In one embodiment, for instance, the liquid powder may comprise a volatile silicone. The term "volatile" refers to those materials having a measurable pressure at ambient conditions. In one embodiment, the volatile silicone has a low molecular weight Volatile polyorganosiloxanes useful herein may be cyclic or linear. Suitable cyclic silicones include polydimethysiloxanes containing from about 4 to about 8 silicon atoms and an equal number of oxygen atoms in the ring (i.e. D4 to D8). The straight chain silicones that are suitable for the composition include those with a viscosity equal to or less than about 5 centistokes.

The cyclic silicones suitable for use are generally known as cyclomethicones. In one embodiment, the volatile silicone is cyclomethicone, more specifically cyclopentasiloxane, a compound sold commercially under the name DOW CORNING 245 (distributed by Dow Corning Corp.).

In another embodiment, the composition comprises a low viscosity dimethicone, for example, a linear polysiloxane. One example of a commercially available low viscosity dimethicone, for instance, is DOW CORNING 200 dimethicone available from the Dow Corning Corp. DOW CORNING 200 dimethicone has a viscosity of about 5 centistoke. Other suitable volatile silicones for use include, for example, cyclomethicones of varying viscosities, e.g., DOW CORNING 244, DOW CORNING 344, and DOW CORNING 345 (commercially available from Dow Corning Corp.); SF-1204 and SF-1202 Silicone Fluids (commercially available from G.E. Silicones), Silicone 7207 and Silicone 7158 (commercially available from Union Carbide Corp.); and SWS-03314 (commercially available from SWS Silicones Corp.).

In one embodiment, especially when the delivery product is to be used in conjunction with an absorbent article, the skin composition may contain a diaper rash agent which may be configured to form at least a partial skin barrier. Suitable compounds that serve as diaper rash agents include zinc oxide, a nonvolatile dimethicone, allantoin, cod liver oil, colloidal oatmeal, kaolin, lanolin, petrolatum, topical starch, or mixtures thereof.

In one embodiment, the skin composition may contain a sunscreen agent. Some examples of sunscreen agents that may by incorporated into the composition are: aminobenzoic acid (PABA), avobenzone, cinoxate, dioxybenzone, homosalate, menthyl anthranilate, octocrylene, octyl methoxycinnamate, octyl salicylate, benzophenone-3, ethylhexy dimethyl PABA, phenylbenzimidole sulfonic acid, benzophenone-4, and trolamine salicylate. The composition may also include but is not limited to all current monographed organic sunscreens both oil and water soluble.

In one embodiment, the skin composition may include an additive that regulates the release of one or more components from the film, in addition to the film itself. Such additives may provide for long term delivery of one or more components contained in the film. The appropriate amount of such an additive will depend on the desired rate and duration of the release. Examples of such additives include water insoluble polymers such as ethylcellulose, acrylic resins, copolymers of methacrylic acid and acrylic acid ethyl ester, polylactic acid, polylactic-co-glycolic acid, polyurethane, polyethylene vinyl acetate copolymer, and polystyrene-butadiene copolymers.

Other additives that may be present in the skin composition include lubricants, plasticizing agents, preservatives, thickeners, emulsion stabilizers, stick formers, suppository formers, coloring agents, chelating agents, fragrances, viscosity controlling agents, and pH-adjusting agents.

Thickeners that may be used in the skin composition include various modified celluloses. For instance, the thickener may comprise ethylcellulose, hydroxypropyl cellulose, carboxymethyl cellulose, hydroxypropylmethyl cellulose, hydroxyethylmethyl cellulose, and combinations thereof. Additionally, fumed silica may serve as a thickener.

The relative amount of the topical skin composition present in the delivery product of the present disclosure can vary dramatically depending upon the particular application and the materials used to construct the product. In general, the skin composition is present in the product in an amount from about 0.5% to about 80% by weight. When the topical skin composition is applied topically to the film, even greater amounts may be present.

For exemplary purposes only, the following is a list of particular skin care actives or medicaments that may be present in the delivery product and exemplary weight percentages: Allantoin, 0.5 to 2 percent; Aluminum hydroxide gel, 0.15 to 5 percent; Calamine, 1 to 25 percent; Cocoa butter, 50 to 80 percent; Cod liver oil, 5 to 13.56 percent; Dimethicone, 1 to 30 percent; Glycerin, 20 to 45 percent; Kaolin, 4 to 20 percent; Lanolin, 12.5 to 50 percent; Petrolatum, 30 to 80 percent; Topical starch, 10 to 80 percent; Zinc acetate, 0.1 to 2 percent; Zinc carbonate, 0.2 to 2 percent; Zinc oxide, 1 to 25 percent.

In order to apply the delivery product to the skin, surface tension only may be used to maintain contact between the delivery product and the skin in a desired area. Although a skin adhesive may be used in certain embodiments, in one embodiment, no such adhesive is present in the product. Skin adhesives, for instance, are not typically needed when the product is used in conjunction with an absorbent article. In particular, the absorbent article can be used to maintain contact between the delivery product and the skin.

As described above, in one embodiment, the delivery product of the present disclosure can be used as an insert in association with an absorbent article. For example, referring to FIGS. 2-5, for exemplary purposes, an absorbent article 20 that may be used in association with the delivery product 10 is shown. The absorbent article 20 may or may not be disposable. In the figures, a diaper is shown. It should be understood, however, that the delivery product is suitable for use with various other absorbent articles intended for personal wear, including but not limited to training pants, swim pants, feminine hygiene products, incontinence products, medical garments, surgical pads and bandages, other personal care or healthcare garments, and the like without departing from the scope of the invention.

By way of illustration only, various materials and methods for constructing absorbent articles such as the article 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 2:
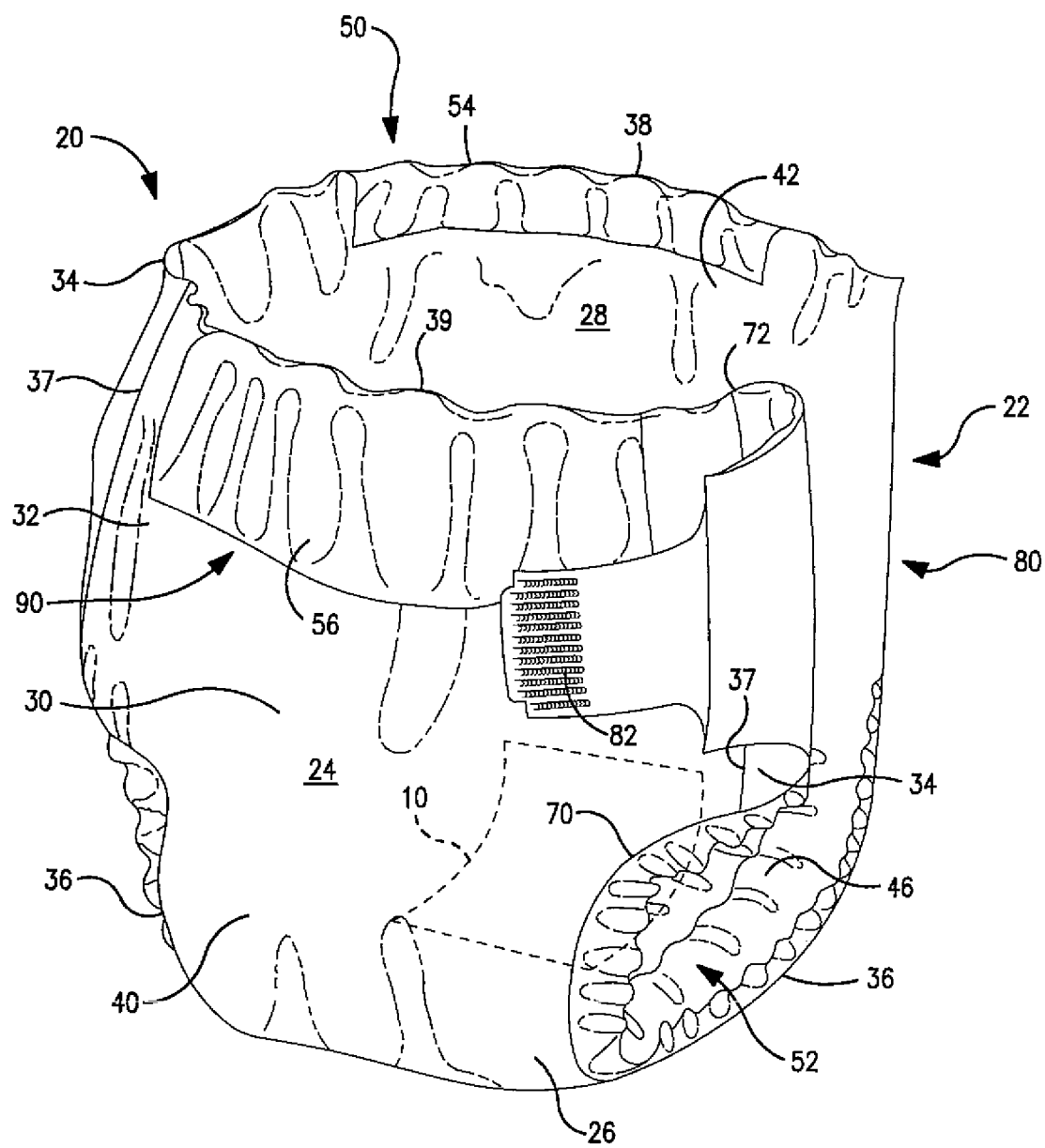
FIG. 2 is a perspective view of one embodiment of an absorbent article that may be used in association with the delivery product of the present disclosure.
Figure 3:
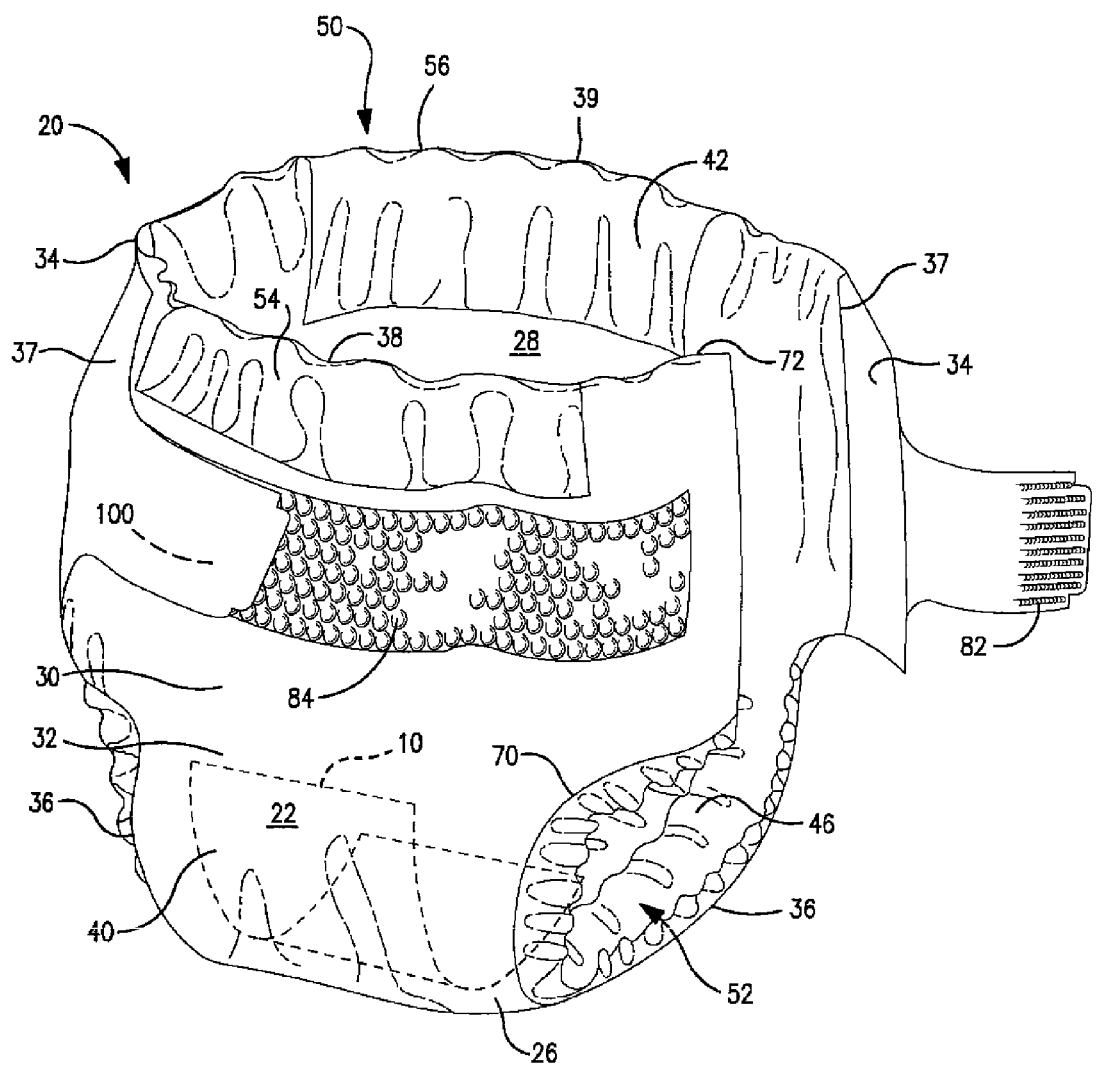
FIG. 3 is another perspective view of the absorbent article illustrated in FIG. 2.
Figure 4:
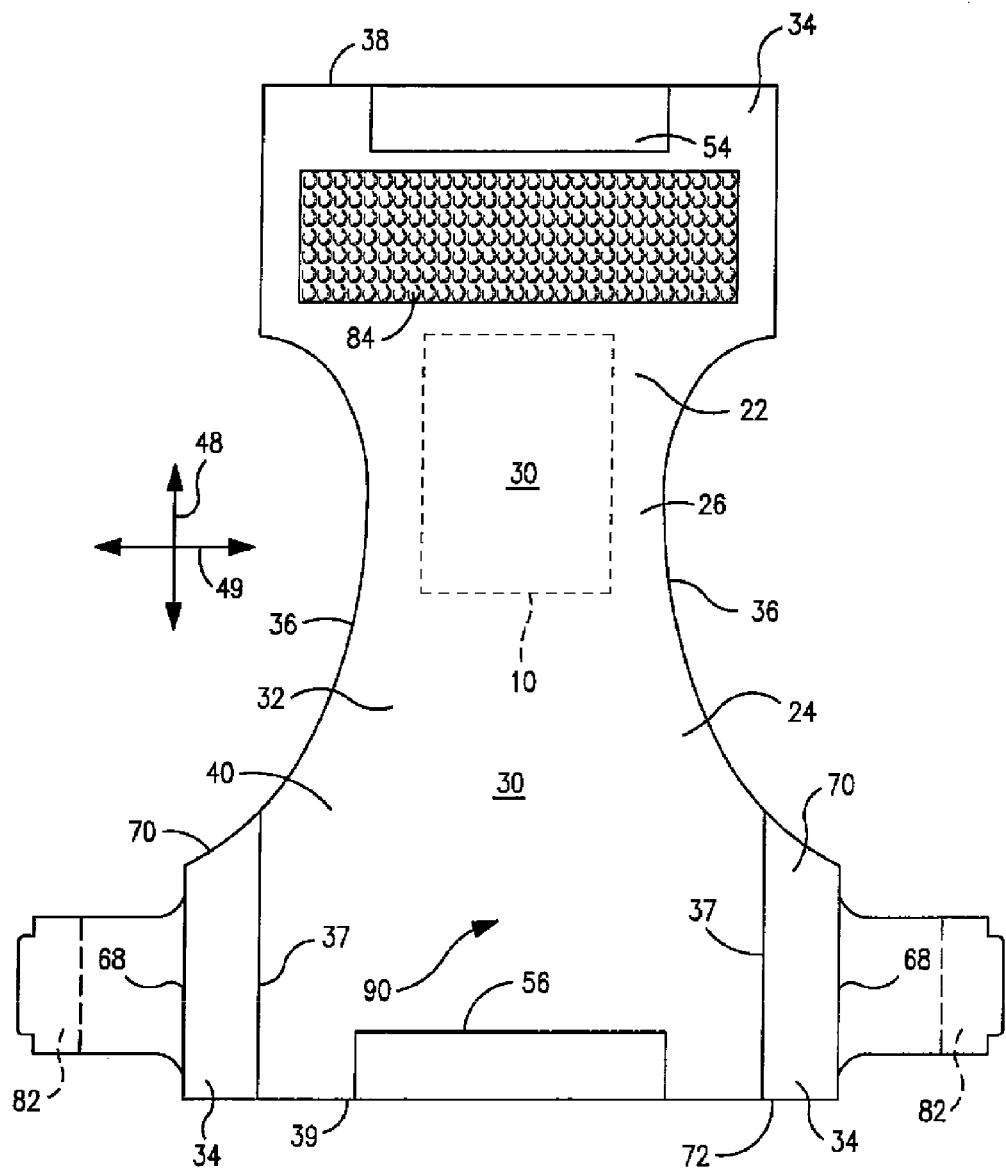
FIG. 4 is a plan view of the exterior surface of the absorbent garment illustrated in FIG. 2.
Figure 5:
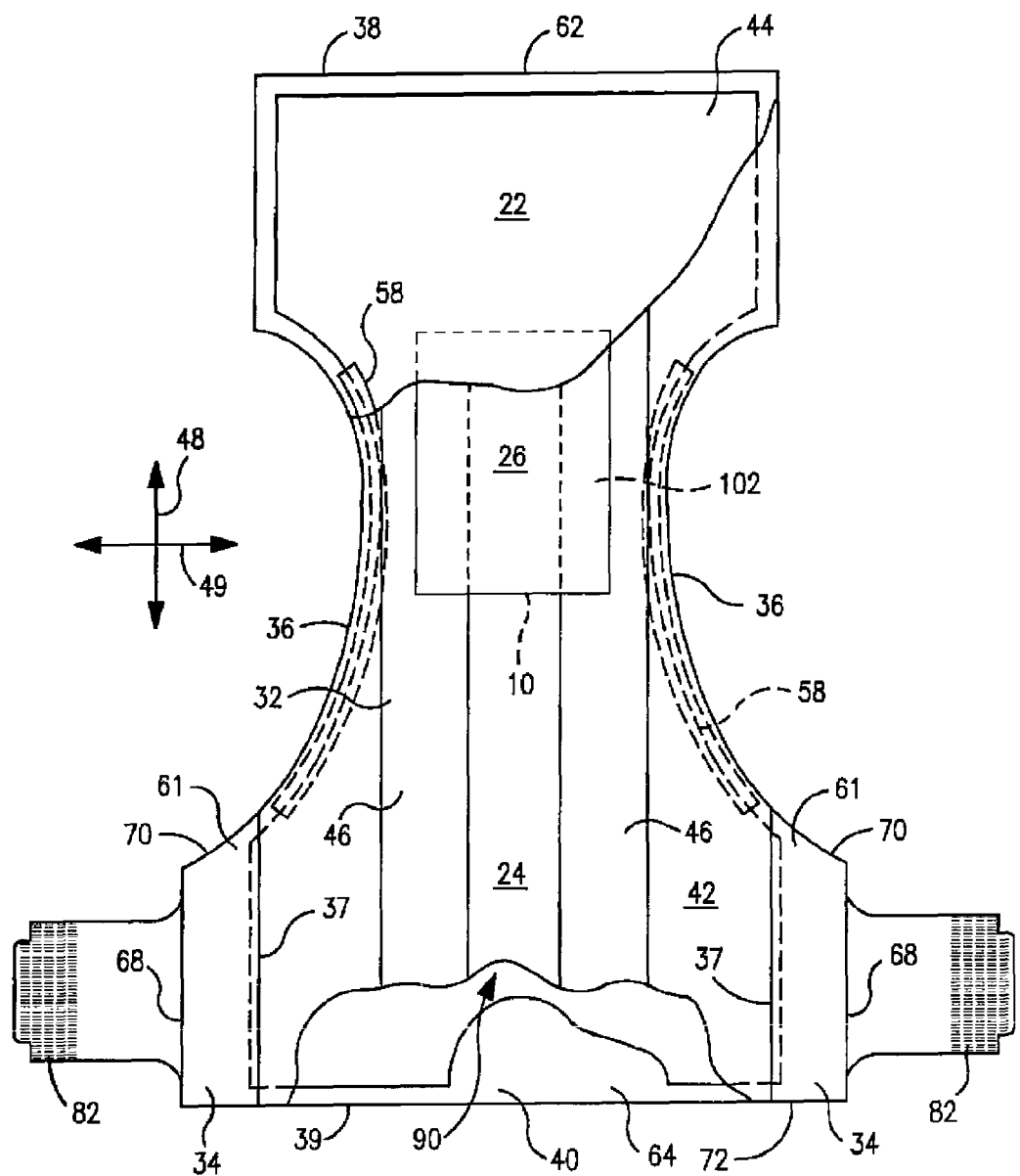
FIG. 5 is a plan view of the absorbent article illustrated in FIG. 2.

An absorbent article 20 is representatively illustrated in FIG. 2 in a partially fastened condition. The absorbent article 20 shown in FIGS. 2 and 3 is also represented in FIGS. 4 and 5 in an opened and unfolded state. Specifically, FIG. 4 is a plan view illustrating the exterior side of the absorbent article 20, while FIG. 5 illustrates the interior side of the absorbent article 20. As shown in FIGS. 4 and 5, the absorbent article 20 defines a longitudinal direction 48 that extends from the front of the article when worn to the back of the article. Opposite to the longitudinal direction 48 is a lateral direction 49.

The absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The absorbent article 20 also defines an inner surface 28 adapted in use (e.g., positioned relative to the other components of the article 20) to be disposed toward the wearer, and an outer surface 30 opposite the inner surface. The front and back regions 22, 24 are those portions of the absorbent article 20, which when worn, wholly or partially cover or encircle the waist or mid-lower torso of the wearer. The crotch region 26 generally is that portion of the absorbent article 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated absorbent article 20 includes a chassis 32, that, in this embodiment, encompasses the front region 22, the back region 24, and the crotch region 26. Referring to FIGS. 2-5, the chassis 32 includes an outer cover 40 and a bodyside liner 42 (FIGS. 2 and 5) that may be joined to the outer cover 40 in a superimposed relation therewith by adhesives, ultrasonic bonds, thermal bonds or other conventional techniques. Referring to FIG. 5, the liner 42 may suitably be joined to the outer cover 40 along the perimeter of the chassis 32 to form a front waist seam 62 and a back waist seam 64. As shown in FIG. 5, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure 44 particularly shown in FIG. 5 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 5 define a partially unattached edge which assumes an upright configuration in at least the crotch region 26 of the absorbent article 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the absorbent article 20 may also suitably include leg elastic members 58 (FIG. 5), as are known to those skilled in the art. The leg elastic members 58 can be operatively joined to the outer cover 40 and/or the bodyside liner 42 and positioned in the crotch region 26 of the absorbent article 20.

In some embodiments, the absorbent article 20 may further include a surge management layer (not shown) which may be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that may be rapidly introduced into the absorbent structure of the article.

As shown in FIGS. 2-5, the absorbent article 20 further includes a pair of opposing elastic side panels 34 that are attached to the back region of the chassis 32. As shown particularly in FIGS. 2 and 3, the side panels 34 may be stretched around the waist and/or hips of a wearer in order to secure the garment in place. As shown in FIGS. 4 and 5, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 2 and 3, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant or absorbent swimwear.

The elastic side panels 34 each have a longitudinal outer edge 68, a leg end edge 70 disposed toward the longitudinal center of the absorbent article 20, and waist end edges 72 disposed toward a longitudinal end of the absorbent article. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. As shown in FIG. 5, the outer edges 68 are generally parallel to the longitudinal direction 48 while the waist end edges 72 are generally parallel to the transverse axis 49. It should be understood, however, that in other embodiments the outer edges 68 and/or the waist edges 72 may be slanted or curved as desired. Ultimately, the side panels 34 are generally aligned with a waist region 90 of the chassis.

The fastening system 80 may include laterally opposite first fastening components 82 adapted for refastenable engagement to corresponding second fastening components 84. In the embodiment shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the embodiment shown in the figures, the fastening components 82 are attached to the side panels 34 along the edges 68. In this embodiment, the fastening components 82 are not elastic or extendable. In other embodiments, however, the fastening components may be integral with the side panels 34. For example, the fastening components may be directly attached to the side panels 34 on a surface thereof.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

As shown in FIGS. 2-5, the absorbent article 20 is placed in association with a delivery device 10 made in accordance with the present disclosure. The delivery device 10, for instance, can be a separate insert that a user manually positions within the absorbent article in the desired location. Having the delivery product 10 serve as an insert also gives control to the user as to when to use the delivery product and when to use similar absorbent articles without the delivery product.

Having the delivery product 10 comprise an insert that is manually inserted in the article also provides advantages to the manufacturer. For example, if the delivery product 10 contains an over-the-counter active ingredient and the absorbent article was sold with the delivery product already in place, various federal and local laws may require that the article be made according to special manufacturing conditions. In particular, the manufacturing facility may need to be certified as an over-the-counter manufacturing facility. By providing the delivery product 10 to consumers separate from the absorbent article, however, no such requirements are needed.

In FIGS. 2-5, the delivery product 10 is shown positioned between the crotch region 26 and the front region 22. In other embodiments, however, the delivery product may be positioned more towards the back region 24. In still other embodiments, the delivery product 10 may be placed around the waist opening or at any other suitable location where skin treatment may be needed.

In the figures, the delivery product 10 is shown having a rectangular shape. It should also be understood, however, that the delivery product 10 can have any suitable shape. In fact, the delivery product 10 may have a shape that conforms to the particular area of the body where treatment is needed.

Figure 6:
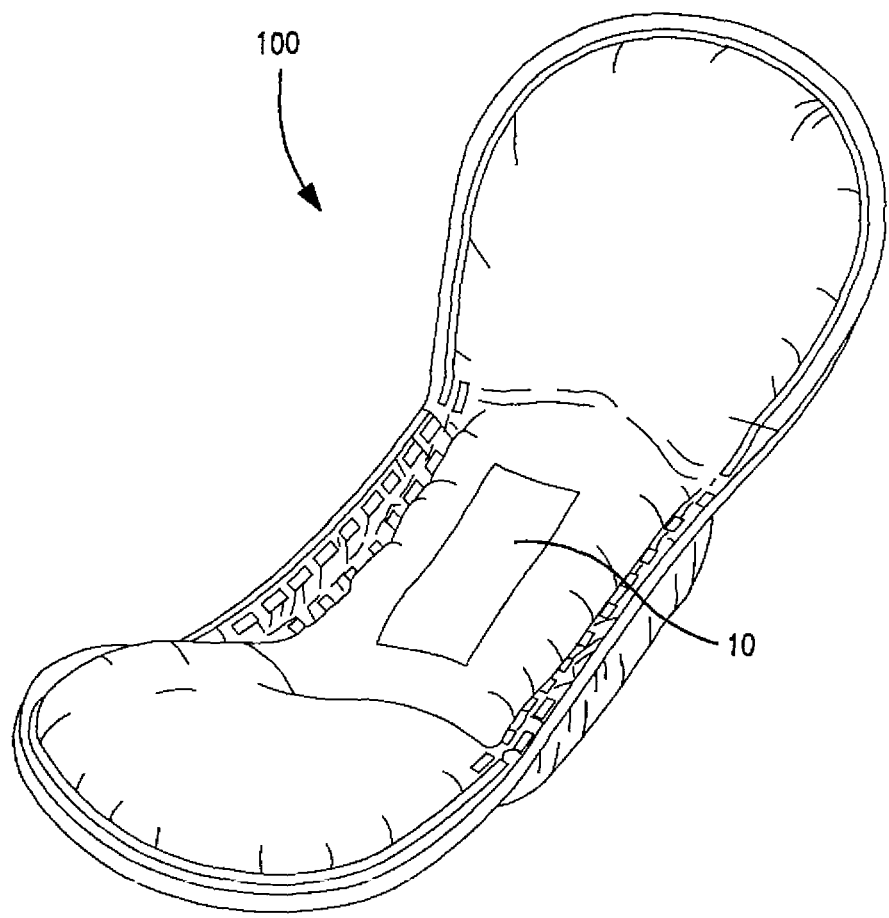
FIG. 6 is a perspective view of one embodiment of a feminine hygiene product that may be used in association with the delivery product of the present disclosure.

In addition to being used in conjunction with a diaper as shown in FIGS. 2-5, the delivery product 10 may be used with any other suitable absorbent article. For instance, referring to FIG. 6, a feminine care pad 100 is shown. Positioned on the interior surface of the pad 100 is the delivery product 10.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A delivery product for topical skin compositions, the delivery product comprising only:
   (a) a film layer having a first surface and a second surface;
   (b) a first releasable backing layer positioned on the first surface of the film layer; and
   (c) optionally a second releasable backing layer positioned on the second surface of the film layer;
   and wherein the film layer comprises:
      a thermo-responsive polymer film, the thermo-responsive polymer film being solid at a temperature of 23° C., the thermo-responsive polymer film comprising an interpenetrating polymer network; a topical skin composition in association with the thermo-responsive polymer film, the topical skin composition containing a skin care active, a medicament or mixtures thereof; and wherein the skin care active or the medicament comprises an antibacterial agent, a deodorant, a skin moisturizer, a cleanser, an anti-itch agent, a cooling agent, a diaper rash agent, or mixtures thereof; and wherein the thermo-responsive polymer film changes properties at a temperature greater than 23° C. but less than about 37° C. so as to cause the solid film to degrade such that when the delivery product is placed in contact with a person's skin, and wherein the thermo-responsive polymer film is configured to increase in temperature and degrade solely by being placed in contact with a user's skin, wherein the solid film degrades by losing structural integrity comprising disintegrating, turning into a liquid, or being absorbed.

2. A delivery product as defined in claim 1, wherein the thermo-responsive polymer film changes properties at a temperature of from about 30° C. to about 34° C.

3. A delivery product as defined in claim 1, wherein the thermo-responsive polymer film comprises a chitosan.

4. A delivery product as defined in claim 1, wherein the thermo-responsive polymer film is substantially water insoluble.

5. A delivery product as defined in claim 1, wherein the skin care active or the medicament comprises a diaper rash agent.

6. A delivery product as defined in claim 1, wherein the delivery product includes the second releasable backing layer.

7. A delivery product as defined in claim 1, wherein, once the thermo-responsive polymer film is placed on a surface at a temperature of 34° C. in an ambient environment, the thermo-responsive polymer film takes at least 30 minutes to completely degrade.

8. A delivery product as defined in claim 1, wherein the thermo-responsive polymer film does not contain a skin adhesive on any surface thereof.

9. A delivery product as defined in claim 1, wherein the skin care active or medicament comprises an antibacterial agent.

10. A system for delivering a topical skin composition comprising:
    an absorbent article configured to be placed adjacent to the skin of a wearer, the absorbent article including an interior surface configured to be placed adjacent to the skin and an opposite exterior surface; and
    an insert that is manually positioned on the interior surface of the absorbent article for contact with the wearer's skin, the insert comprising a delivery product defined in claim 1.

11. A system as defined in claim 10, wherein the absorbent article comprises a diaper or a pant.

12. A system as defined in claim 10, wherein the absorbent article comprises a feminine hygiene pad.

13. A system as defined in claim 10, wherein the absorbent article comprises an adult incontinence garment.

14. A system as defined in claim 10, wherein the absorbent article comprises a wound dressing.

15. A system as defined in claim 11, wherein the skin care active or medicament contained in the topical skin composition comprises a diaper rash agent.

16. A system as defined in claim 10, wherein the thermo-responsive polymer film is substantially water insoluble.

17. A system as defined in claim 10, wherein the skin care active or the medicament comprises an antibacterial agent.

18. A system as defined in claim 10, wherein the releasable backing layer is removed from the thermo-responsive polymer film when the insert is manually positioned on the interior surface of the absorbent article.

19. A delivery product as defined in claim 1, wherein the topical skin composition is incorporated into the thermo-responsive polymer film.

20. A delivery product as defined in claim 3, wherein the chitosan has been made thermally sensitive by the addition of a salt.

21. A delivery product as defined in claim 3, wherein the chitosan has been combined with a polyol salt.

22. A delivery product as defined in claim 1, wherein the first releasable backing layer and the second optional releasable backing layer comprise a polymer film or paper layer coated with a release material.

* * * * *